United States Patent
Uchida (10) Patent No.: US 10,359,373 B2
(45) Date of Patent: Jul. 23, 2019

(54) MEASURING DEVICE

(71) Applicant: Earthnix-M, Inc., Tokyo (JP)

(72) Inventor: Hiroshi Uchida, Tokyo (JP)

(73) Assignee: Earthnix-M, Inc., Tokyo (JP)

( * ) Notice: Subject to any disclaimer, the term of this patent is extended or adjusted under 35 U.S.C. 154(b) by 0 days.

(21) Appl. No.: 15/631,615

(22) Filed: Jun. 23, 2017

(65) Prior Publication Data

US 2018/0003650 A1 Jan. 4, 2018

(30) Foreign Application Priority Data

Jun. 29, 2016 (JP) ................................. 2016-128397

(51) Int. Cl.
| | |
|---|---|
| *G01N 22/04* | (2006.01) |
| *H01Q 13/02* | (2006.01) |
| *G01S 7/03* | (2006.01) |
| *G01F 23/284* | (2006.01) |
| *G01S 13/88* | (2006.01) |
| *G01N 22/00* | (2006.01) |

(52) U.S. Cl.
CPC ........... *G01N 22/04* (2013.01); *G01F 23/284* (2013.01); *G01N 22/00* (2013.01); *G01S 7/03* (2013.01); *G01S 13/88* (2013.01); *H01Q 13/02* (2013.01)

(58) Field of Classification Search
CPC ...... G01N 22/04; G01N 22/00; G01N 27/223; G01N 33/246; H01Q 13/02; G01F 23/284
See application file for complete search history.

(56) References Cited

U.S. PATENT DOCUMENTS

2015/0101405 A1    4/2015 Gorenflo et al.

FOREIGN PATENT DOCUMENTS

| | | | |
|---|---|---|---|
| EP | 3 165 883 A1 | 5/2017 | |
| EP | 3165883 A1 * | 5/2017 | ........... G01F 23/284 |
| JP | 11-142352 A | 5/1999 | |
| WO | 2004/046663 A1 | 6/2004 | |

OTHER PUBLICATIONS

EP 3165883 A, Skowaisa et al, Machine Translation, Applicant Admitted Prior Art cited on IDS of Oct. 31, 2017.*
EP_3165883_A1_Skowaisa_05_2017_Machine Translation.*
Communication dated Sep. 14, 2017 from the European Patent Office in counterpart application No. 17177777.4.

* cited by examiner

*Primary Examiner* — Jermele M Hollington
*Assistant Examiner* — Suresh K Rajaputra
(74) *Attorney, Agent, or Firm* — Sughrue Mion, PLLC (57) ABSTRACT

A measuring device that makes it possible to improve precision and stability is provided.

In a measuring device 50, a microwave receiving unit 52 is disposed behind a microwave transmitting unit 51 with respect to a powder object 2, and the microwave transmitting unit 51 and the microwave receiving unit 52 are each enclosed by a waveguide box. A waveguide box 6 for the transmitting unit is smaller than a waveguide box 8 for the receiving unit, and is enclosed by the waveguide box 8 for the receiving unit. An opening portion 7 of the waveguide box 6 and an opening portion 9 of the waveguide box 8 are mounted on a flat window material 5, and are aligned. The window material 5 is in contact with the powder object 2. Microwaves 3 transmitted from the microwave transmitting unit 51 are reflected by the powder object 2, are received, as scattered microwaves 4, by the microwave receiving unit 52, and are measured.

20 Claims, 5 Drawing Sheets

MEASURING DEVICE

BACKGROUND OF THE INVENTION

1. Field of the Invention

The present invention relates to a measuring device that measures an object to be measured by using microwaves.

Hitherto, in measuring the water content of, for example, sheet-like objects, such as pulp or boards; powder objects (such as sand or flour); chips; or tea leaves, a transmission-type water content measuring device using microwaves or a capacitance-type water content measuring device has been used. In some cases, a reflection-type water content measuring device using microwaves has also been used in measuring the water content of sand.

For example, a microwave moisture meter described in Patent Literature 1 below includes a density measuring unit that measures the density of a powder object to be measured by irradiating the powder object to be measured with γ rays at a region that is the same as a region that is irradiated with microwaves. A γ-ray source of the density measuring unit projects from an inner wall of a hopper.

2. Description of the Related Art

PTL

[Patent Literature 1] Japanese Unexamined Patent

SUMMARY OF THE INVENTION

However, in the existing microwave moisture meter, as mentioned above, the γ-ray source of the density measuring unit projects from the inner wall of the hopper. Therefore, samples accumulate there, and a so-called bridge may occur. Consequently, in measuring water content, measurement precision and stability cannot be improved.

In addition, a transmission-type water content measuring device of a type that measures and corrects bulk density and that measures a powder object on a conveyor is expensive. Further, in level measurement by a radar system, close range measurement cannot be performed. Even in underground structure inspections using underground radar or inspections of arrangement of reinforcements of concrete, measurement precision and stability cannot be improved.

The present invention has been proposed in view of the above-described circumstances. That is, it is an object of the present invention to provide a measuring device that makes it possible to improve measurement precision and stability by receiving reflected waves from all directions.

To this end, a measuring device according to the present invention makes measurement as a result of a microwave transmitted from a transmitting unit being reflected at an object to be measured and being received as a reflected wave by a receiving unit, wherein the receiving unit is disposed behind the transmitting unit with respect to the object to be measured.

In the measuring device according to the present invention, a horn antenna or a waveguide box is provided at the transmitting unit or the receiving unit.

In the measuring device according to the present invention, a horn antenna or a waveguide box is provided at each of the transmitting unit and the receiving unit.

In the measuring device according to the present invention, the horn antenna or the waveguide box provided at the transmitting unit is disposed at an inner side of the horn antenna or the waveguide box provided at the receiving unit.

In the measuring device according to the present invention, a second receiving unit is provided at the transmitting unit.

The measuring device according to the present invention has the above-described structures. That is, in a reflection-type measuring instrument, by separately providing the transmitting unit and the receiving unit and disposing the receiving unit behind the transmitting unit with respect to an object to be measured, it is possible to efficiently and stably receive reflected waves from all directions. In addition, since the transmitting unit and the receiving unit are separately provided, measurement can be made by performing a combination of, for example, power measurement, phase measurement, and Doppler measurement. Therefore, measurement stability can be improved.

In the measuring device according to the present invention, for example, an array antenna or a horn antenna is provided at the transmitting unit or the receiving unit. This structure makes it possible to make precise measurement including measurement of information regarding directions of reflected waves from all hemispherical directions. In addition, in measuring the water content of powder objects, it is possible to receive reflected waves from all directions and improve measurement precision and stability.

In the measuring device according to the present invention, a second receiving unit is provided at the transmitting unit. By this structure, providing the two receiving units with different functions such as a power measurement function, a phase measurement function, a Doppler measurement function, or a pulse Doppler function makes it possible to make measurement in a combination of various modes. In this case, by switching measurement modes, it is possible to measure the thickness and the water content of an object to be measured. For example, the measuring device can be used in, for example, level measurement, close range measurement, or radar for preventing involvement when a vehicle turns left or right. Further, even in underground structure inspections using underground radar, inspections of arrangement of reinforcements of concrete, or examinations of soil water content distribution by being mounted on a flying object, measurement precision and stability can be improved.

DESCRIPTION OF THE PREFFERED EMBODIMENT

Measuring devices according to embodiments of the present invention are described below with reference to the drawings. The measuring devices are reflection-type measuring devices that measure backscattered waves in microwave application measurement. The measuring devices include a microwave transmitting unit and a microwave receiving unit, with the microwave receiving unit being disposed behind the microwave transmitting unit with respect to an object to be measured. Microwaves are transmitted in the direction of an object to be measured, and reflected waves from the object to be measured are measured. The measuring devices are used in level measurement and water content measurement. In the direction below, in FIG. 1, the direction in which microwaves are transmitted towards an object to be measured from the measuring device is defined as the front, and the direction in which the microwaves are reflected is defined as the back.

Figure 1:
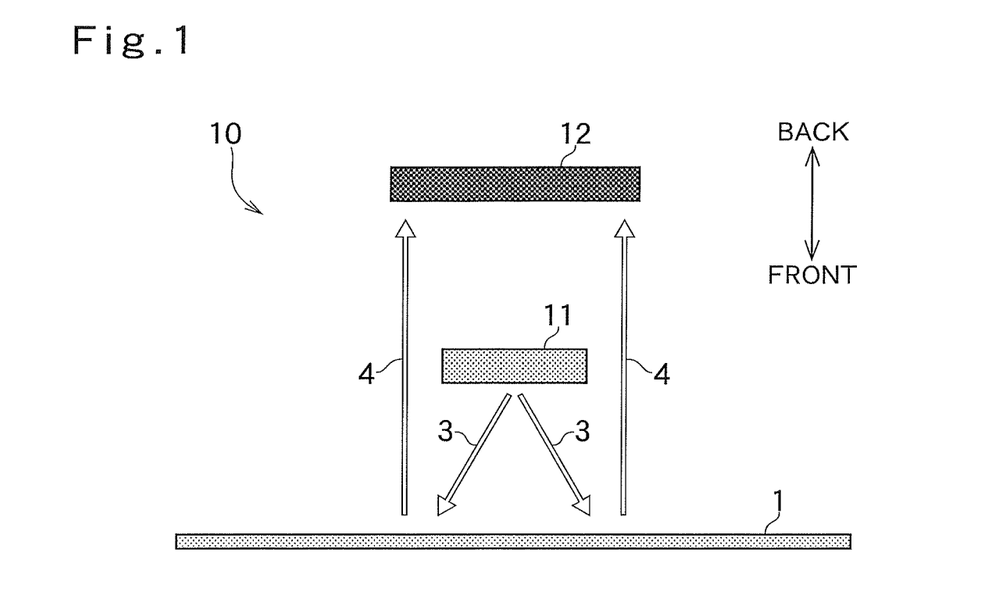
FIG. 1 is a schematic front sectional view of a measuring device according to a first embodiment of the present invention.

In a measuring device 10 according to a first embodiment shown in FIG. 1, a microwave transmitting unit 11 and a microwave receiving unit 12 are each an array antenna. The microwave transmitting unit 11 is disposed apart from and faces a membrane/board 1, which is an object to be measured. On the other hand, the microwave receiving unit 12 is further away from the membrane/board 1 than the microwave transmitting unit 11, and is disposed behind the microwave transmitting unit 11. The microwave receiving unit 12 is formed larger than the microwave transmitting unit 11 so as to be large enough to be capable of receiving reflected waves from the membrane/board 1. Microwave transmission waves 3 transmitted from the microwave transmitting unit 11 strike the membrane/board 1 and are reflected by the membrane/board 1. Then, as backscattered waves, scattered microwaves 4 are received by the microwave receiving unit 12.

Figure 2:
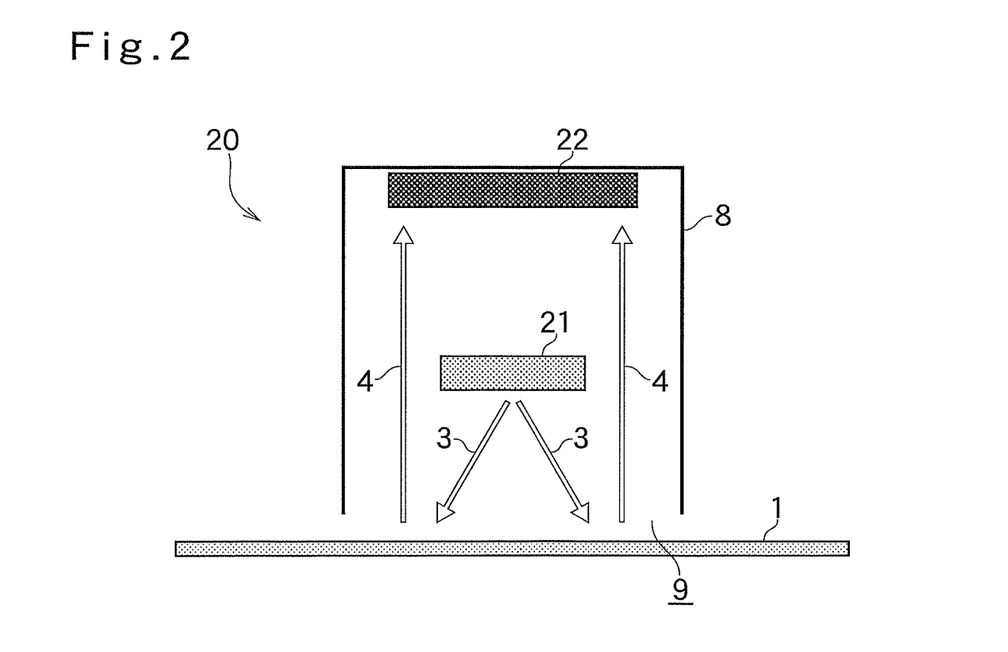
FIG. 2 is a schematic front sectional view of a measuring device according to a second embodiment of the present invention.

In a measuring device 20 according to a second embodiment shown in FIG. 2, a microwave transmitting unit 21 and a microwave receiving unit 22 are each an array antenna. However, unlike in the measuring device 10 according to the first embodiment, the microwave receiving unit 22 is, along with the microwave transmitting unit 21, enclosed by a waveguide box 8 for the receiving unit. The waveguide box 8 for the receiving unit has an opening portion 9 where a front side is open. The opening portion 9 faces and is disposed close to a membrane/board 1. At an inner side of the waveguide box 8 for the receiving unit, the microwave transmitting unit 21 is disposed apart from and faces the membrane/board 1. On the other hand, the microwave receiving unit 22 is formed larger than the microwave transmitting unit 21 so as to be large enough to be capable of receiving scattered microwaves 4, which are reflected waves. The microwave receiving unit 22 is disposed further away from the membrane/board 1 than the microwave transmitting unit 21 and behind the microwave transmitting unit 21. The microwave receiving unit 22 is mounted on a bottom portion of the waveguide box 8 for the receiving unit. That is, surrounding portions of the microwave receiving unit 22 excluding a portion facing the membrane/board 1 are, along with the microwave transmitting unit 21, enclosed by the waveguide box 8 for the receiving unit. Microwave transmission waves 3 transmitted from the microwave transmitting unit 21 strike the membrane/board 1 and are reflected by the membrane/board 1. Then, as backscattered waves, the scattered microwaves 4 are received by the microwave receiving unit 22.

Figure 3:
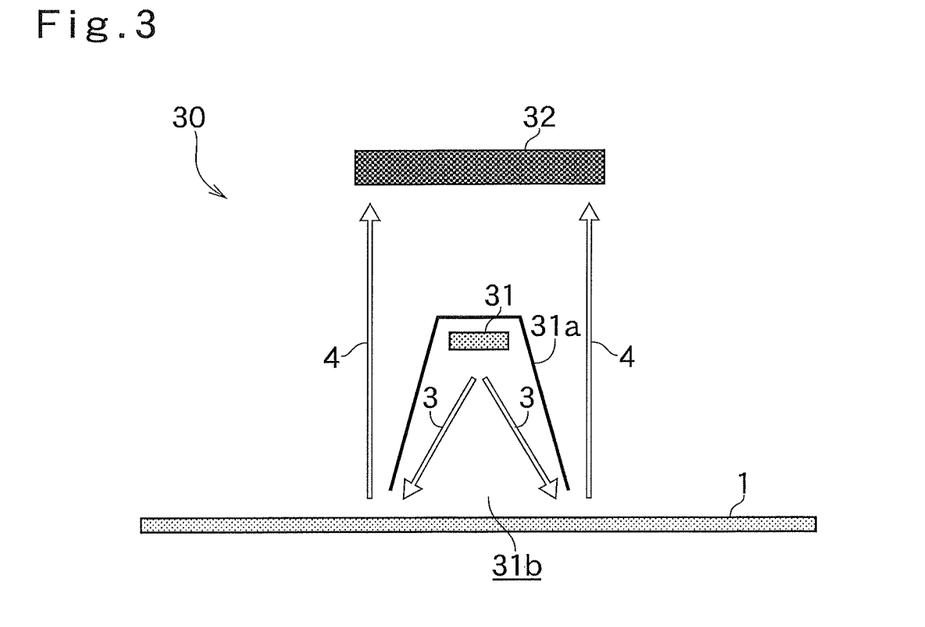
FIG. 3 is a schematic front sectional view of a measuring device according to a third embodiment of the present invention.

In a measuring device 30 according to a third embodiment shown in FIG. 3, a microwave receiving unit 32 is an array antenna. However, unlike in the measuring device 10 according to the first embodiment, a microwave transmitting unit 31 is a horn antenna 31a. The horn antenna 31a is such that a horn opening portion 31b is disposed close to a membrane/board 1. On the other hand, the microwave receiving unit 32 is formed larger than the horn opening portion 31b so as to be large enough to be capable of receiving scattered microwaves 4. The microwave receiving unit 32 is disposed further away from the membrane/board 1 than the microwave transmitting unit 31 and behind the microwave transmitting unit 31. Microwave transmission waves 3 transmitted from the microwave transmitting unit 31 propagate in the horn antenna 31a, and strike the membrane/board 1 and are reflected by the membrane/board 1. Then, as backscattered waves, the scattered microwaves 4 are received by the microwave receiving unit 32.

Figure 4:
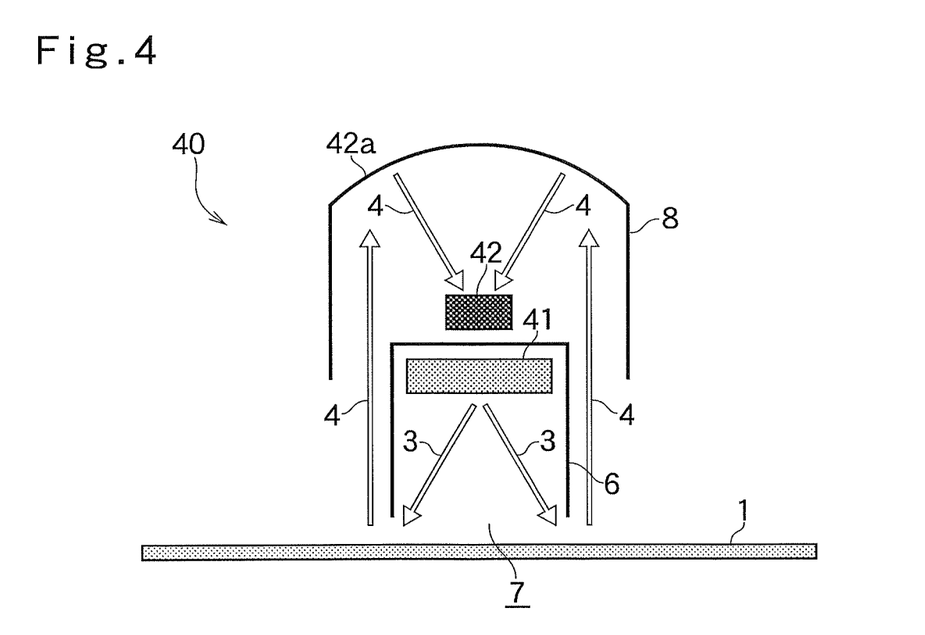
FIG. 4 is a schematic front sectional view of a measuring device according to a fourth embodiment of the present invention.

In a measuring device 40 according to a fourth embodiment shown in FIG. 4, a microwave transmitting unit 41 is an array antenna. However, unlike in the measuring device 10 according to the first embodiment, the microwave transmitting unit 41 is surrounded by a waveguide box 6 for the transmitting unit, and a microwave receiving unit 42 is a reflector antenna and is surrounded by a waveguide box 8 for the receiving unit. An opening portion 7 of the waveguide box 6 for the transmitting unit faces and is close to a membrane/board 1. In the waveguide box 6 for the transmitting unit, the microwave transmitting unit 41 is disposed apart from and faces the membrane/board 1, and is mounted on a bottom portion of the waveguide box 6 for the transmitting unit. That is, surrounding portions of the microwave transmitting unit 41 excluding a portion facing the membrane/board 1 are surrounded by the waveguide box 6 for the transmitting unit. On the other hand, the microwave receiving unit 42 is further away from the membrane/board 1 than the microwave transmitting unit 41, is disposed behind the microwave transmitting unit 41, and is disposed on a back-surface side of the waveguide box 6 for the transmitting unit. A reflecting mirror 42a of the microwave receiving unit 42 is formed larger than the microwave transmitting unit 41 and the waveguide box 6 for the transmitting unit so as to be large enough to be capable of receiving reflected waves. The waveguide box 8 for the receiving unit is mounted on an end of the reflecting mirror 42a. Microwave transmission waves 3 transmitted from the microwave transmitting unit 41 propagate in the waveguide box 6 for the transmitting unit, and strike the membrane/board 1 and are reflected by the membrane/board 1. Then, as backscattered waves, scattered microwaves 4 propagate in the waveguide box 8 for the receiving unit, are reflected by the reflecting mirror 42a, and are received by the microwave receiving unit 42.

Figure 5A:
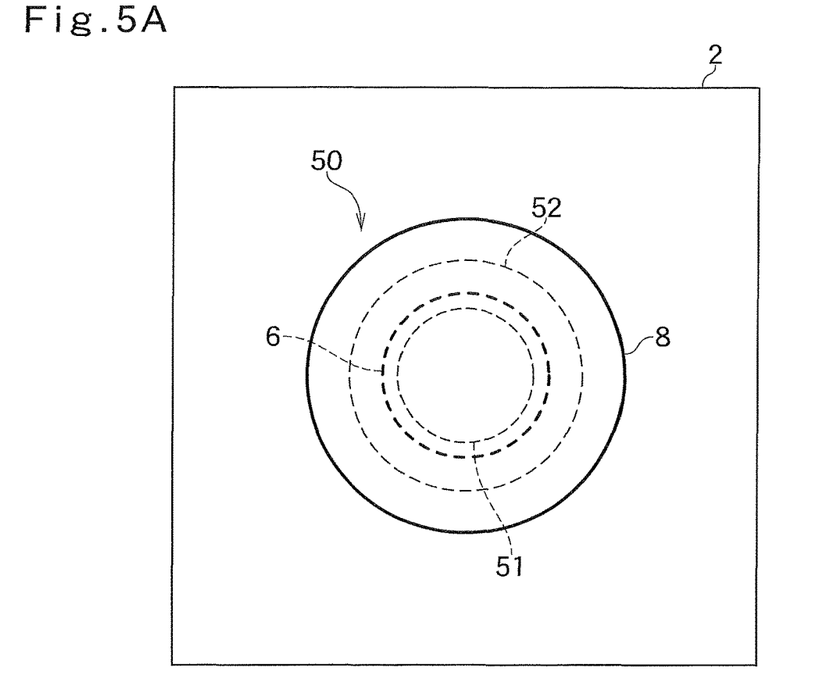
FIG. 5A is a schematic plan through view of a measuring device according to a fifth embodiment of the present invention.
Figure 5B:
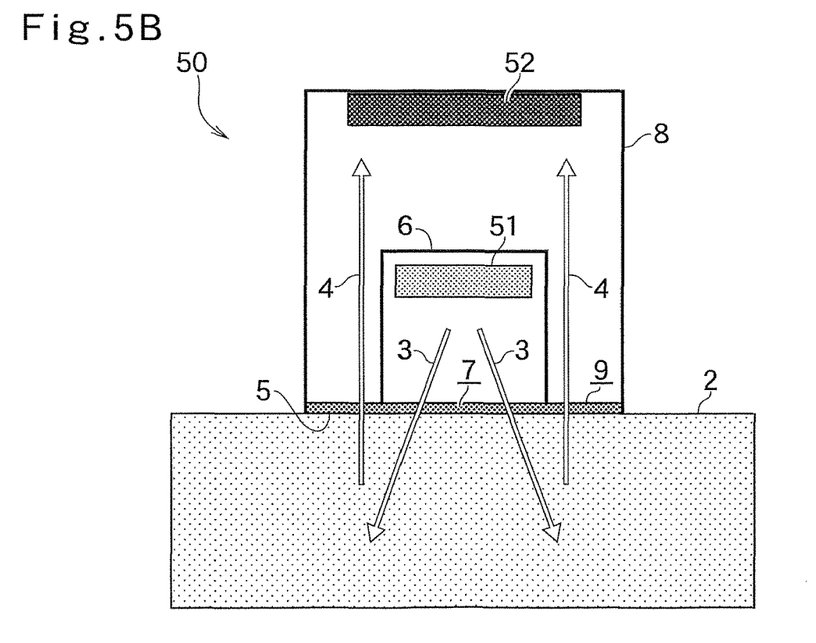
FIG. 5B is a schematic front sectional view of the measuring device according to the fifth embodiment of the present invention.

In a measuring device 50 according to a fifth embodiment shown in FIGS. 5A and 5B, a microwave transmitting unit 51 and a microwave receiving unit 52 are each an array antenna. However, unlike in the measuring device 10 according to the first embodiment, the microwave transmitting unit 51 and the microwave receiving unit 52 are each enclosed by a waveguide box. A waveguide box 6 for the transmitting unit is smaller than a waveguide box 8 for the receiving unit, and is enclosed by the waveguide box 8 for the receiving unit at an inner side of the waveguide box 8 for the receiving unit. An opening portion 7 of the waveguide box 6 and an opening portion 9 of the waveguide box 8 are aligned with and mounted on a flat window material 5. The window material 5 is in contact with a powder object 2, which is an object to be measured. In the waveguide box 6 for the transmitting unit, the microwave transmitting unit 51 is disposed apart from and faces the powder object 2, and is mounted on a bottom portion of the waveguide box 6 for the transmitting unit. That is, surrounding portions of the microwave transmitting unit 6 excluding a portion facing the powder object 2 are enclosed by the waveguide box 6 for the transmitting unit. On the other hand, the microwave receiving unit 52 is formed larger than the waveguide box 6 for the transmitting unit so as to be large enough to be capable of receiving scattered microwaves 4. The microwave receiving unit 52 is further away from the powder object 2 than the microwave transmitting unit 51, and is disposed behind the microwave transmitting unit 51. The microwave receiving unit 52 is mounted on a bottom portion of the waveguide box 8 for the receiving unit. That is, enclosed portions of the microwave receiving unit 52 excluding a portion facing the powder object 2 are enclosed by the waveguide box 8 for the receiving unit. Microwave transmission waves 3 transmitted from the microwave transmitting unit 51 propagate in the waveguide box 6 for the transmitting unit, and strike the powder object 2 and are reflected by the powder object 2. Then, as backscattered waves, the scattered microwaves 4 propagate in the waveguide box 8 for the receiving unit and are received by the microwave receiving unit 52. The measuring device 50 is used in inspections of arrangement of reinforcements and underground structure inspections in addition to level measurement and water content measurement. According to the measuring device 50, the scattered microwaves 4 in a range of 360 degrees around an opening portion 7 serving as an irradiation opening portion, can be efficiently received.

Figure 6A:
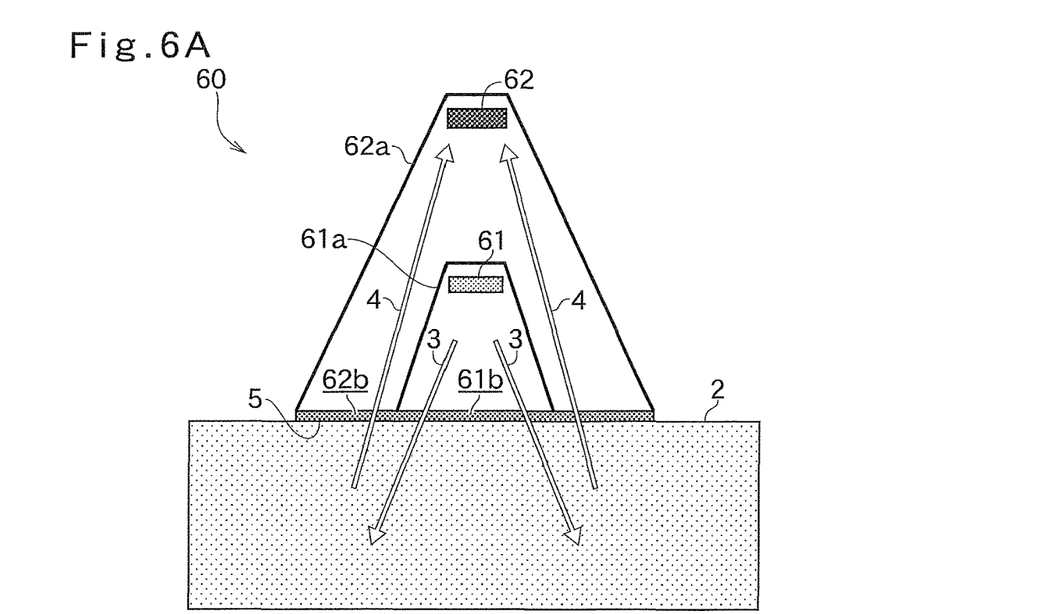
FIG. 6A is a schematic front sectional view of a measuring device according to a sixth embodiment of the present invention.
Figure 6B:
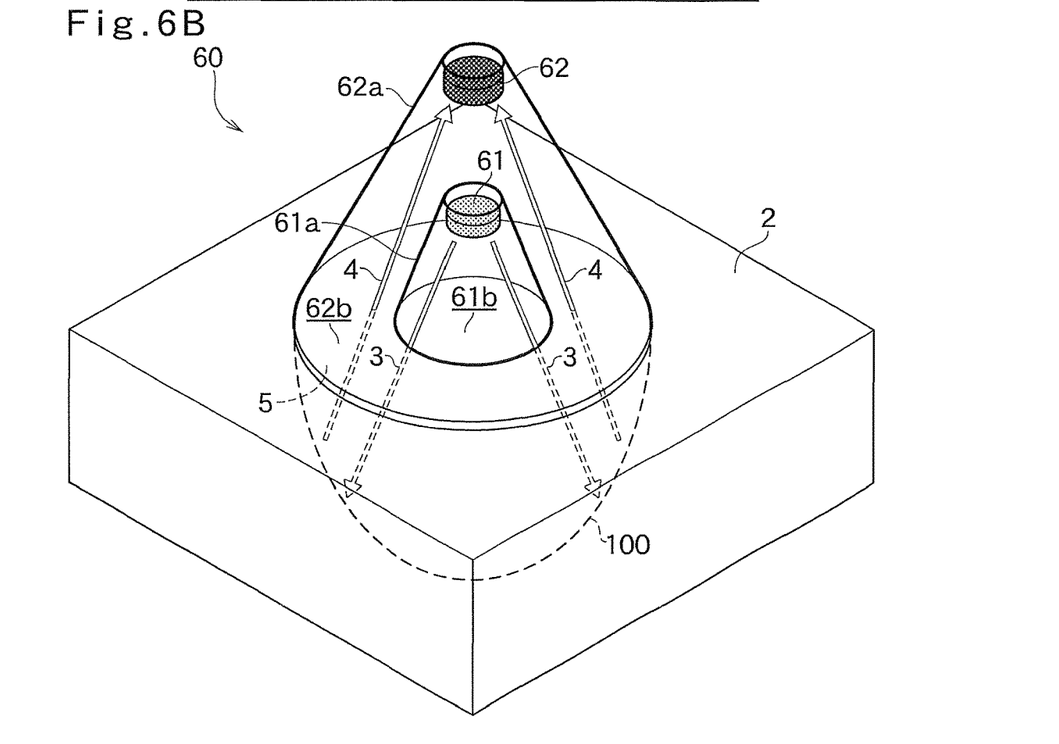
FIG. 6B is a schematic perspective through view of a measuring device according to the sixth embodiment of the present invention.

In a measuring device 60 according to a sixth embodiment shown in FIGS. 6A and 6B, unlike in the measuring device 10 according to the first embodiment, a microwave transmitting unit 61 and a microwave receiving unit 62 are each a horn antenna. A horn antenna 61a for the transmitting unit is smaller than a horn antenna 62a for the receiving unit, and is surrounded by the horn antenna 62a for the receiving unit at an inner side of the horn antenna 62a for the receiving unit. A horn opening portion 61b of the horn antenna 61a and a horn opening portion 62b of the horn antenna 62a are aligned with and mounted on a flat window material 5. The window material 5 is in contact with a powder object 2. Microwave transmission waves 3 transmitted from the microwave transmitting unit 61 propagate in the horn antenna 61a for the transmitting unit, and strike the powder object 2 and are reflected by the powder object 2. Then, as backscattered waves, scattered microwaves 4 propagate in the horn antenna 62a for the receiving unit, and are received by the microwave receiving unit 62. The measuring device 60 is used in inspections of arrangement of reinforcements and underground structure inspections in addition to level measurement and water content measurement. According to the measuring device 60, the radiated scattered microwaves 4 in a hemispherical direction, that is, the scattered microwaves 4 reflected at a region 100 centered on a hemispherical shape of the powder object 2 can be efficiently received.

Figure 7:
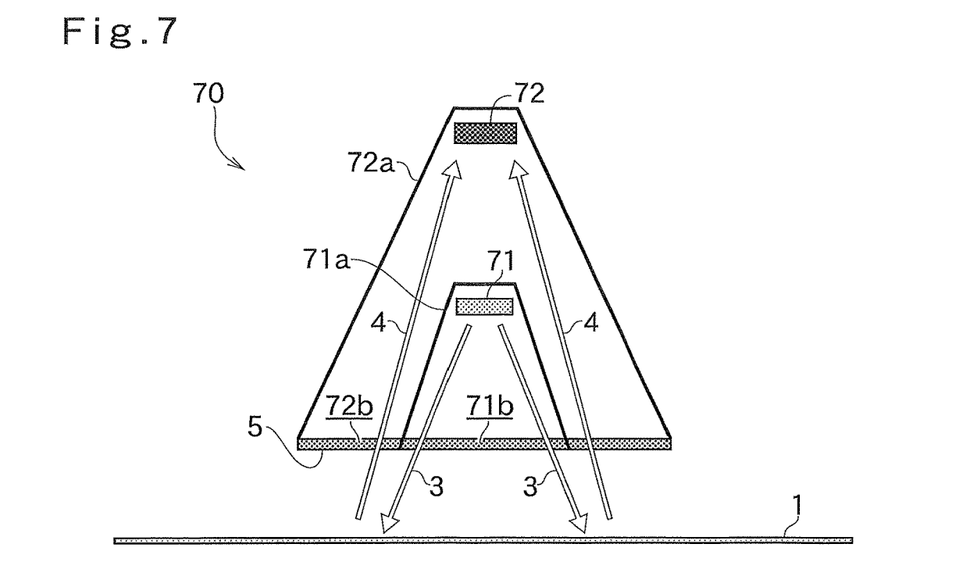
FIG. 7 is a schematic front sectional view of a measuring device according to a seventh embodiment of the present invention.

In a measuring device 70 according to a seventh embodiment shown in FIG. 7, unlike in the measuring device 10 according to the first embodiment, a microwave transmitting unit 71 and a microwave receiving unit 72 are each a horn antenna. A horn antenna 71a for the transmitting unit is smaller than a horn antenna 72a for the receiving unit, and is surrounded by the horn antenna 72a for the receiving unit at an inner side of the horn antenna 72a for the receiving unit. A horn opening portion 71b of the horn antenna 71a and a horn opening portion 72b of the horn antenna 72a are aligned with and mounted on a flat window material 5. The window material 5 is disposed apart from a membrane/board 1. Microwave transmission waves 3 transmitted from the microwave transmitting unit 71 propagate in the horn antenna 71a for the transmitting unit, and strike the membrane/board 1 and are reflected by the membrane/board 1. Then, as backscattered waves, scattered microwaves 4 propagate in the horn antenna 72a for the receiving unit, and are received by the microwave receiving unit 72. The measuring device 70 is used in inspections of arrangement of reinforcements and underground structure inspections in addition to level measurement and water content measurement.

Figure 8:
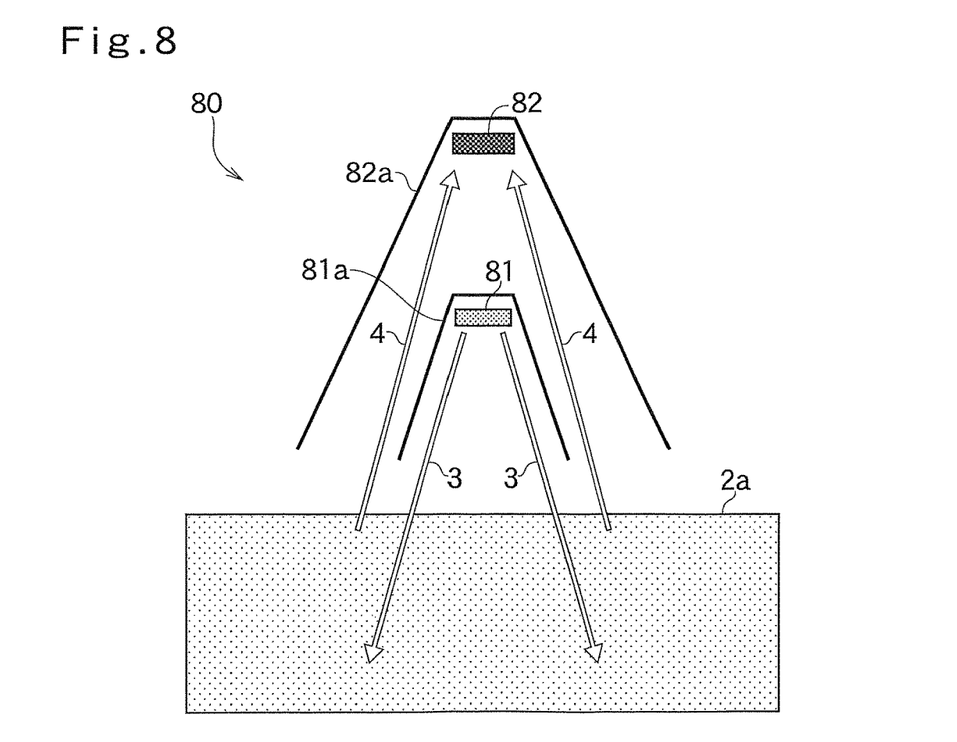
FIG. 8 is a schematic front sectional view of a measuring device according to an eighth embodiment of the present invention.

In a measuring device 80 according to an eighth embodiment shown in FIG. 8, unlike in the measuring device 10 according to the first embodiment, a microwave transmitting unit 81 and a microwave receiving unit 82 are each a horn antenna. A horn antenna 81a for the transmitting unit is smaller than a horn antenna 82a for the receiving unit, and is enclosed by the horn antenna 82a for the receiving unit at an inner side of the horn antenna 82a for the receiving unit. A horn opening portion 81b of the horn antenna 81a and a horn opening portion 82b of the horn antenna 82a are aligned with each other, and are disposed apart from, for example, soil/plant 2a, which is an object to be measured. Microwave transmission waves 3 transmitted from the microwave transmitting unit 81 propagate in the horn antenna 81a for the transmitting unit, and strike the soil/plant 2a and are reflected by the soil/plant 2a. Then, as backscattered waves, scattered microwaves 4 propagate in the horn antenna 82a for the receiving unit, and are received by the microwave receiving unit 82. The measuring device 80 can be used in, for example, examination of soil water content distribution by being mounted on a flying object, in addition to level measurement and water content measurement. According to the measuring device 80, the radiated scattered microwaves 4 in a hemispherical direction, that is, the scattered microwaves 4 reflected at a region 100 centered on a hemispherical shape of the soil/plant 2a can be efficiently received. According to the eighth embodiment, with increasing distance of the measuring device 80 from the soil/plant 2a, the scattered microwaves 4 reflected at a disc-shaped region of the soil/plant 2a are received.

In each of the above-described embodiments, array antenna elements may be disposed in a linear arrangement or in a planar arrangement. The horn antennas may be, for example, a straight horn type, a step type, a multi-flare type, a flare-iris type, or a dielectric loading type. The horn antennas may have a pyramidal shape or a conical shape. Examples of the reflector antenna include a parabolic antenna, an offset parabolic antenna, and a horn reflector. The waveguide box for the transmitting unit and the waveguide box for the receiving unit may be either rectangular-shaped or circular. The size and thickness of the membrane/ board 1 may be arbitrarily selected. The shape and size of a container of the powder object 2 may be arbitrarily selected.

As described above, according to each embodiment, the microwave transmitting units 11, 21, 31, 41, 51, 61, 71, and 81, serving as reflection-type measuring instruments, are provided separately from the microwave receiving units 12, 22, 32, 42, 52, 62, 72, and 82, respectively. By disposing the microwave receiving units 12, 22, 32, 42, 52, 62, 72, and 82 behind the microwave transmitting units 11, 21, 31, 41, 51, 61, 71, and 81, respectively, with respect to the membrane/board 1 or the powder object 2, it is possible to efficiently and stably receive the scattered microwaves 4 from all directions. In addition, since the microwave transmitting units 11, 21, 31, 41, 51, 61, 71, and 81 and the microwave receiving units 12, 22, 32, 42, 52, 62, 72, and 82 are separately provided, measurement can be made by performing a combination of, for example, power measurement, phase measurement, and Doppler measurement, and can improve measurement stability. Further, by using, for example, array antennas or horn antennas, it is possible to make including measurement of information regarding directions of reflected waves from all hemispherical directions. In particular, in measuring the water content of the powder object 2, it is possible to receive the scattered microwaves 4 from all directions and improve measurement precision and stability.

In each of the above-described embodiments, the microwave transmitting units 11, 21, 31, 41, 51, 61, 71, and 81 may be provided with a second microwave receiving unit (not shown). That is, when the microwave receiving units 12, 22, 32, 42, 52, 62, 72, and 82 and the second microwave receiving units have different functions, it is possible to make measurement in a combination of various modes, such as a power measurement mode, a phase measurement mode, a Doppler measurement mode, and a pulse Doppler mode. In this case, by switching measurement modes, it is possible to measure the thickness and the water content of the membrane/board 1 or the powder object 2. For example, in level measurement, the measuring device can be used in short range measurement or radar for preventing involvement when a vehicle turns left or right. Further, for example, even in underground structure inspections by using underground radar, inspections of arrangement of reinforcements of concrete, or examinations of soil water content distribution by being mounted on a flying object, measurement precision and stability can be improved.

Further, it is possible to correct bulk density by combination with a γ-ray reflection-type density meter (not shown). In addition, it is possible to make precise and stable measurement with a weak ray source by combination with a γ-ray reflection-type density meter.

Although embodiments according to the present invention are described in detail, the present invention is not limited to the above-described embodiments. Various changes in design can be made without departing from the matters described in the claims. For example, the present invention is applicable to milling, tea manufacture, chemistry, paper and pulp, steel, non-ferrous materials, building materials, concrete plants, civil engineering sites, agriculture, or grain; water content measurement of sheet-like objects such as paper or boards, powder objects such as sand or wheat, chips, or tea leaves; underground inspections or level measurement of, for example, liquid surfaces; measurement of soil water content; or close range radar measurement.

What is claimed is:

1. A measuring device configured to perform a measurement using a microwave transmitted from a transmitting unit, reflected by an object to be measured and received as a reflected wave by a receiving unit,
    wherein the receiving unit is disposed behind the transmitting unit with respect to the object to be measured,
    wherein a receiving area of the receiving unit is formed larger than a transmitting area of the transmitting unit so as to be large enough to be capable of receiving reflected waves from the object to be measured, and
    wherein said receiving area of the receiving unit is void of shielding elements provided for shielding part of the reflected wave.

2. The measuring device according to claim 1, wherein a horn antenna or a waveguide box is provided at the transmitting unit or the receiving unit.

3. The measuring device according to claim 1, wherein a horn antenna or a waveguide box is provided at each of the transmitting unit and the receiving unit.

4. The measuring device according to claim 3, wherein the horn antenna or the waveguide box provided at the transmitting unit is disposed at an inner side of the horn antenna or the waveguide box provided at the receiving unit.

5. The measuring device according to claim 1, wherein a second receiving unit is provided at the transmitting unit.

6. The measuring device according to claim 2, wherein a second receiving unit is provided at the transmitting unit.

7. The measuring device according to claim 3, wherein a second receiving unit is provided at the transmitting unit.

8. The measuring device according to claim 4, wherein a second receiving unit is provided at the transmitting unit.

9. A measuring device configured to perform a measurement using a microwave transmitted from a transmitting unit, reflected by an object to be measured and received as a reflected wave by a receiving unit,
    wherein the measuring device consists essentially of the transmitting unit and the receiving unit,
    wherein the receiving unit is disposed behind the transmitting unit with respect to the object to be measured.

10. The measuring device according to claim 9, wherein a horn antenna or a waveguide box is provided at the transmitting unit or the receiving unit.

11. The measuring device according to claim 9, wherein a horn antenna or a waveguide box is provided at each of the transmitting unit and the receiving unit.

12. The measuring device according to claim 11, wherein the horn antenna or the waveguide box provided at the transmitting unit is disposed at an inner side of the horn antenna or the waveguide box provided at the receiving unit.

13. The measuring device according to claim 9, wherein a second receiving unit is provided at the transmitting unit.

14. The measuring device according to claim 10, wherein a second receiving unit is provided at the transmitting unit.

15. The measuring device according to claim 11, wherein a second receiving unit is provided at the transmitting unit.

16. The measuring device according to claim 12, wherein a second receiving unit is provided at the transmitting unit.

17. The measuring device according to claim 13, wherein the first receiving unit and the second receiving unit have different functions.

18. The measuring device according to claim 16, wherein the first receiving unit and the second receiving unit have different functions.

19. The measuring device according to claim 18, wherein the different functions are selected from the group consisting of a power measurement function, a phase measurement function, a Doppler measurement function, and a pulse Doppler function.

20. The measuring device according to claim 12, wherein a flat window material is provided as a component of the measuring device, and (i) an opening portion of the horn antenna or the waveguide box provided at the transmitting unit and (ii) an opening portion of the horn antenna or the waveguide box provided at the receiving unit are aligned with and mounted on the flat window material.

* * * * *